(12) United States Patent
Lattanzi et al.

(10) Patent No.: US 11,051,711 B2
(45) Date of Patent: Jul. 6, 2021

(54) NONINVASIVE DETERMINATION OF ELECTRICAL PROPERTIES OF TISSUES AND MATERIALS USING MAGNETIC RESONANCE MEASUREMENTS

(71) Applicant: NEW YORK UNIVERSITY, New York, NY (US)

(72) Inventors: Riccardo Lattanzi, New York, NY (US); Daniel K. Sodickson, New York, NY (US); José E. Cruz Serralles, Cambridge, MA (US); Athanasios Polymeridis, Moscow (RU); Luca Daniel, Cambridge, MA (US); Jacob K. White, Cambridge, MA (US)

(73) Assignee: New York University, New York, NY (US)

( * ) Notice: Subject to any disclaimer, the term of this patent is extended or adjusted under 35 U.S.C. 154(b) by 526 days.

(21) Appl. No.: 15/494,384

(22) Filed: Apr. 21, 2017

(65) Prior Publication Data
US 2017/0303813 A1    Oct. 26, 2017

Related U.S. Application Data

(60) Provisional application No. 62/326,569, filed on Apr. 22, 2016.

(51) Int. Cl.
*A61B 5/055*     (2006.01)
*G01R 33/46*     (2006.01)
(Continued)

(52) U.S. Cl.
CPC .......... *A61B 5/055* (2013.01); *A61B 1/00011* (2013.01); *A61B 5/0004* (2013.01);
(Continued)

(58) Field of Classification Search
None
See application file for complete search history.

(56) References Cited

U.S. PATENT DOCUMENTS

| 2012/0150458 | A1  | 6/2012 | Sodickson et al. |
| 2014/0103925 | A1* | 4/2014 | Hancu ............ G01R 33/48 |
|              |     |        | 324/309 |
| 2016/0054262 | A1  | 2/2016 | Sodickson et al. |

OTHER PUBLICATIONS

Schmidt, "A New Approach for Electrical Properties Estimation Using a Global Integration Equation and Improvements Using High Permittivity Materials" Dec. 1, 2015, Journal of Magnetic Resonance (Year: 2015).*

(Continued)

*Primary Examiner* — Douglas X Rodriguez
(74) *Attorney, Agent, or Firm* — Foley & Lardner LLP

(57) ABSTRACT

A plurality of stimulations is transmitted to tissue or other material using one or more transmitters. The plurality of signals associated with the excited tissue and the transmitted stimulations are measured. The measured signals are processed to generate field-related quantities, such as B1+ and/or MR signal maps. Field-related quantities are generated also from simulation, by calculating the one or more incident fields from a simulator model of the one or more transmitters and assuming a given distribution of electrical properties in the tissue or other material. Field-related quantities generated from simulation and experimental procedures are compared to each other. The assumed electrical properties distribution is updated and the procedure is repeated iteratively until the difference between simulated and experimental field-related quantities is smaller than a threshold.

16 Claims, 11 Drawing Sheets
(9 of 11 Drawing Sheet(s) Filed in Color)

(51) Int. Cl.
  A61B 1/00    (2006.01)
  A61B 5/00    (2006.01)
  G01R 33/48   (2006.01)
  G01R 33/24   (2006.01)
  G01R 33/56   (2006.01)
(52) U.S. Cl.
  CPC .......... *A61B 5/0013* (2013.01); *G01R 33/246* (2013.01); *G01R 33/4616* (2013.01); *G01R 33/48* (2013.01); *G01R 33/56* (2013.01); *A61B 2576/02* (2013.01)

(56) References Cited

OTHER PUBLICATIONS

Association of Radio Industries and Businesses (ARIB), "Specific Absorption Rate (SAR) Estimation for Cellular Phone", ARIB Standard Version 1.0, ARIB STD-T56, Jan. 27, 1998, 73 pages.

Balidemaj, E., et al., "CSI-EPT: A Contrast Source Inversion Approach for Improved MRI-Based Electric Properties Tomography", IEEE Transactions on Medical Imaging, Sep. 2015, 34(9):1788-1796.

Brown, B.H., et al., "Electrical impedance tomography; the construction and application to physiological measurement of electrical impedance images", Medical Progress Through Technology, 1987, 13(2):69-75.

Christ, A., et al., "The Virtual Family—development of surface-based anatomical models of two adults and two children for dosimetric simulations," Phys. Med. Biol., 2010, 55(2):N23-N38.

Duan, Q., et al., "Characterization of a dielectric phantom for high-field magnetic resonance imaging applications", Med. Phys., Oct. 2014, 41(10):102303-1-6.

Gencer, N.G., et al., "Electrical impedance tomography using induced and injected currents", Clin. Phys. Physiol. Meas., 1992, 13(Suppl. A):95-99.

Ianniello, C., et al., "Design and Construction of a Tissue-Mimicking Phantom to Validate Electrical Properties Mapping Techniques Based on Magnetic Resonance", 1st URSI Atlantic Radio Science Conference, 2015, 1 page.

Ianniello, C., et al., "Sugar free tissue-mimicking MRI phantoms for improved signal-to-noise ratio," Proc. Intl. Soc. Mag. Reson. Med., 2016, v. 24, 2 pages.

Katscher, U., et al., "Determination of Electric Conductivity and Local SAR Via B1 Mapping", IEEE Transactions on Medical Imaging, Sep. 2009, 28(9):1365-1374.

Kreutz-Delgado, K., "The Complex Gradient Operator and the CR-Calculus", University of California San Diego: Department of Electrical and Computer Engineering, Jun. 25, 2009, 74 pages.

Leuze, C., "Construction and testing of a realistic head phantom for assessment of radiofrequency power deposition in MRI", University of Leipzig thesis, Nov. 13, 1980, 181 pages.

The Metabolomics Innovation Centre, "Human Metabolome Database: 1H NMR Spectrum (HMDB0000258)", <http://www.hmdb.ca/spectra/nmr_one_d/1293>, no date, 5 pages.

Pierpaoli, C., et al., "Polyvinylpyrrolidone (PVP) water solutions as isotropic phantoms for diffusion MRI studies", Proc. Intl. Soc. Mag. Reson. Med., 2009, 17:1414.

Polimeridis, A.G., et al., "Stable FFT-JVIE solvers for fast analysis of highly inhomogeneous dielectric objects", Journal of Computational Physics, 2014, 269:280-296.

Sarlls, J.E., et al., "Calibrated Diffusion Phantom for 7T MRI", Proc. Intl. Soc. Mag. Reson. Med., 2014, 22:1243.

Schmidt, R., et al., "A new approach for electrical properties estimation using a global integral equation and improvements using high permittivity materials", Journal of Magnetic Resonance, 2016, 262:8-14.

Sodickson, D.K., et al., "Local Maxwell Tomography Using Transmit-Receive Coil Arrays for Contact-Free Mapping of Tissue Electrical Properties and Determination of Absolute RF Phase," Proc. Intl. Soc. Mag. Reson. Med., 2012, 20:387.

Stuchly, M.A., et al., "Measurement of Radio Frequency Permittivity of Biological Tissues with an Open-Ended Coaxial Line: Part II—Experimental Results", IEEE Transactions on Microwave Theory and Techniques, Jan. 1982, 30(1):87-92.

Varnykh, V.L., "Actual Flip-Angle Imaging in the Pulsed Steady State: A Method for Rapid Three-Dimensional Mapping of the Transmitted Radiofrequency Field", Magnetic Resonance in Medicine, 2007, 57(1):192-200.

Villena, J.F., et al., "Fast Electromagnetic Analysis of MRI Transmit RF Coils Based on Accelerated Integral Equation Methods", IEEE Transactions on Biomedical Engineering, Nov. 2016, 63(11):2250-2261.

Villena, J.F., et al., "Magnetic Resonance Specific Integral Equation Solver Based on Precomputed Numerical Green Functions", 2013 International Conference on Electromagnetics in Advanced Applications, 2013, pp. 724-727.

Wiggins, G.C., et al., "A Highly Decoupled 8 Channel Transmit-Receive Loop Array for 7T with Diverse B1 Profiles", Proc. Intl. Soc. Mag. Reson. Med., 2012, 20:309.

Giannakopoulos, I.I., et al., "Magnetic-resonance-based electrical property mapping using Global Maxwell Tomography with an 8-channel head coil at 7 Tesla: a simulation study", IEEE Transactions on Biomedical Engineering, 2020, 12 pages.

Serralles, J.E.C., et al., "Noninvasive Estimation of Electrical Properties From Magnetic Resonance Measurements via Global Maxwell Tomography and Match Regularization", IEEE Transactions on Biomedical Engineering, Jan. 2020, 67(1):3-15.

\* cited by examiner

Ground Truth

Initial Guess

NONINVASIVE DETERMINATION OF ELECTRICAL PROPERTIES OF TISSUES AND MATERIALS USING MAGNETIC RESONANCE MEASUREMENTS

CROSS-REFERENCE TO RELATED APPLICATIONS

This application claims the benefit of priority to U.S. Patent Application No. 62/326,569 filed on Apr. 22, 2016, the entire content of which is incorporated herein by reference.

This invention was made with government support under Grant No. 1453675 awarded by the National Science Foundation and Grant No. P41 EB017183 awarded by the National Institutes of Health. The government has certain rights in the invention.

FIELD

The present disclosure generally relates to magnetic resonance techniques for determining and studying electrical properties of materials or tissues.

BACKGROUND

Electrical properties provide an important window into tissue structure and function. For example, electrical properties may be employed as biomarkers for cancers and other pathologies, as the electrical conductivity and permittivity of cancerous tissue has been found to be greater than those of normal tissues. Various measurement approaches have been proposed to study electrical properties.

SUMMARY

Certain embodiments of the present disclosure relate to apparatuses, methods, and computer-readable media with instructions thereon for determination of electrical properties of tissues or materials.

According to an embodiment, a method for determining at least one electrical property of at least one target includes transmitting, to the at least one target, a plurality of stimulations via one or more transmitters, measuring signals associated with the stimulated target, processing the measured signals to obtain electromagnetic field-related quantities, and comparing the electromagnetic field-related quantities obtained from processing the measured signals to simulated electromagnetic field-related quantities. In at least one embodiment, the method for determining at least one electrical property of at least one target is an iterative method in which, when the process-derived electromagnetic field-related quantities deviate by a predetermined threshold or more from the simulated electromagnetic field-related quantities, the simulation updates its estimate of electrical property values, and then simulates new electromagnetic-field related quantities. The new simulated electromagnetic-field relates quantities are compared to the measured values (i.e., those obtained from processing), and this process is repeated until the deviation is less than the predetermined threshold value.

According to another embodiment, a non-transitory computer readable medium includes instructions thereon that are accessible by a processing arrangement. When the processing arrangement executes the instructions, the processing arrangement is configured to cause one or more transmitters to transmit, to at least one target, a plurality of stimulations, measure signals associated with the stimulated target, process the measured signals to obtain electromagnetic field-related quantities, and compare the electromagnetic field-related quantities obtained from processing the measured signals to simulated electromagnetic field-related quantities.

According to a further embodiment, a system for determining at least one electrical property of at least one target includes one or more transmitters configured to transmit a plurality of stimulations to the at least one target, a signal detector configured to measure signals associated with the stimulated target, a computing device configured to process the measured signals to obtain electromagnetic field-related quantities, and compare the electromagnetic field-related quantities obtained from processing the measured signals to simulated electromagnetic field-related quantities.

Additional features, advantages, and embodiments of the present disclosure are apparent from consideration of the following detailed description, drawings, and claims. Moreover, it is to be understood that both the foregoing summary of the present disclosure and the following detailed description are exemplary and intended to provide further explanation without limiting the scope of the present disclosure and the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other objects, aspects, features, and advantages of the disclosure will become more apparent and better understood by referring to the following description taken in conjunction with the accompanying drawings, in which.

DETAILED DESCRIPTION

Figure 1:
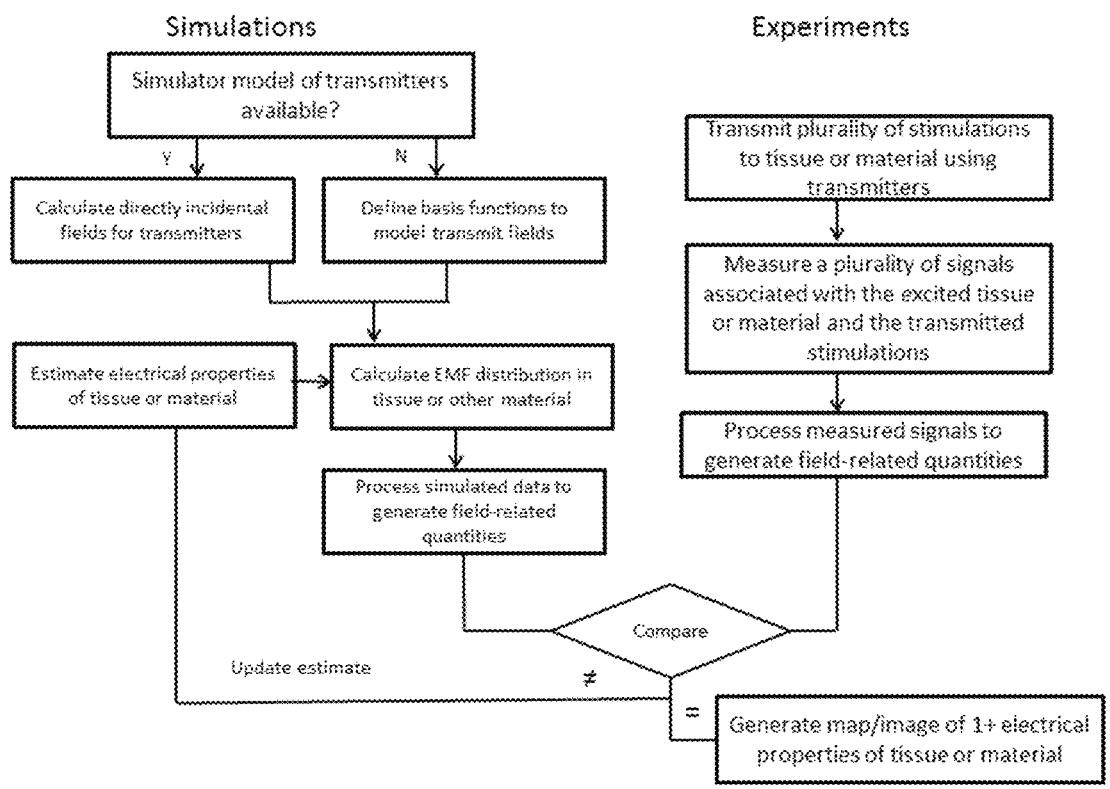
FIG. 1 illustrates a method for determining electrical properties according to an embodiment.

In the following detailed description, reference is made to the accompanying drawings, which form a part hereof. In the drawings, similar symbols typically identify similar elements, unless context dictates otherwise. The illustrative embodiments and/or implementations described in the detailed description, drawings, and claims are not meant to be limiting. Other embodiments and/or implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of ways, all of which are explicitly contemplated and made part of this disclosure.

Electrical property estimation has long been pursued also as a possible contrast mechanism for biological tissue. In fact, electrical properties provide an important window into tissue structure and function. For example, electrical properties could be employed as biomarkers for cancer (and other pathologies), since the electrical conductivity and permittivity of cancerous tissue has been found to be greater than those of normal tissues.

Conventional hyperthermia treatment techniques typically assume a fixed tissue conductivity across patients and tumor sites. However, the assumption of fixed tissue conductivity may result in lower tumor temperatures, and therefore lead to less effective treatment. Further, taking into account subject-specific data offers the possibility for tailored treatment. For example, knowledge of subject-specific dielectric properties of cancerous tissues could be used for reliable hyperthermia treatment planning, by allowing accurate calculation of the radiofrequency (RF) power deposited in tissue (usually expressed in terms of specific absorption rate (SAR)) from electromagnetic (EM) field exposures.

Studies have suggested that electrical properties may be employed for non-invasive detection of scar tissue in the myocardium. Further, elevations in tissue permittivity have been associated with the process of fibrosis formation during radiation therapy treatment. Thus, electrical properties may be employed in radiotherapy monitoring, because timely knowledge of the presence of fibrosis may justify administering fibrosis regressing agents to prevent extensive tissue remodeling or even organ failure.

In particular, the availability of a patient's internal electrical information may allow patient-specific noninvasive estimation of the quantity and distribution of the SAR. Estimating patient-specific SAR properties in a non-invasive manner is difficult to accomplish in magnetic resonance (MR) imaging (MRI) generally, and high-field and ultra-high-field MRI in particular. Since patient-specific SAR cannot be monitored reliably, a 'worst-case' set of assumptions is used when calibrating the system input power during ultra-high-filed MRI. Thus, in many actual treatment sessions, the actual SAR will be less than the assumed worse-case. That is, the full potential of such ultra-high-field MRIs is not realized or taken advantage when using a conservative calibration settings according to the 'worst case' scenario, to further reduce risks to the patient. Being able to monitor patient-specific SAR may allow for exploitation of the full potential of ultra-high-field MRI by allowing methods that currently are not implemented to avoid risks to patient safety. In other words, patient-specific monitoring may provide information to enable decisions about how and when to increase power while substantially avoiding harm to the patient, to obtain better MRI contrasts and higher image resolution, for example. Additionally, SAR calculations based on measured electrical properties may be useful for RF safety assessment, beyond MRI. As required by the Federal Communications Commission (FCC) and other regulatory bodies, SAR must be measured for all RF emitting devices prior to the devices entering the consumer market, to prevent excessive RF energy deposition into the body.

Finally, the field of nondestructive testing (NDT) would benefit considerably from the capability to map electrical properties of materials noninvasively. In fact, such capacity could potentially enhance all applications that typically use NDT, including forensic engineering, mechanical engineering, petroleum engineering, electrical engineering, civil engineering, systems engineering, aeronautical engineering, medicine, and art.

Although numerous ex vivo or in situ measurements of electrical properties of animal tissue have been made over time, experimental access to in vivo electrical properties of human tissue has remained extremely limited, and fundamental questions regarding the origin and distribution of these properties remain unanswered.

Various techniques have been proposed to study electrical properties of human tissue, but none have achieved reliable and non-invasive mapping of the spatial distribution of tissue electrical properties. Such techniques include electrical impedance tomography (EIT), which is based on surface measurement after an injection of currents. EIT, while viewed as being promising for detection of cancers, has been hampered by the need to solve a difficult inverse problem. As a further example, MR provides cross-sectional information about selected magnetic field distributions, and has recently been used in the low-frequency MREIT technique, which solves for conductivity based on the fields produced by applied currents.

As a further example, the MR Electrical Properties Tomography (MR-EPT) technique uses measurements of field curvature to estimate RF conductivity and permittivity from Maxwell equations. The aforementioned MR-based approaches, however, do not supply certain important information, such as the distribution of the absolute RF phase and magnetization. Further, the MR-EPT technique relies upon symmetry assumptions, which require a specific transmit-receive coil and, furthermore, do not hold up at high frequency, which is precisely where accurate electrical property determination is most critical. Further, the MR-EPT technique requires calculating numerical derivative of noisy data, which limits the achievable spatial resolution and causes artifacts at boundaries between regions with different electrical properties.

A more general technique, Local Maxwell Tomography (LMT), does not rely on symmetry assumptions and uses multiple MR-based measurements of local field curvature to derive unknown electrical property distributions, effectively inverting Maxwell's equations. However, LMT is significantly constrained by edge artifacts and low effective resolution due to reliance on local numerical derivatives. As a further example, generalized LMT is an extension of LMT which takes into account the presence of boundary regions and materials with anisotropic electrical property tensors, as described in U.S. Patent Application Publication No. 2016/0054262 to Sodickson et al., entitled "System, method and computer-accessible medium for providing generalized local Maxwell tomography for mapping of electrical property gradients and tensors," published on Feb. 25, 2016. However, generalized LMT may have drawbacks such as low effective resolution due to reliance on local numerical derivatives relative to the systems and methods set forth herein.

Such approaches do not permit accurate determination of tissue electrical properties non-invasively and with clinically-usable spatial resolution. U.S. patent application Ser. No. 13/314,105 to Sodickson et al., filed on Dec. 7, 2011, describes various approaches including local Maxwell equations, and is incorporated herein by reference in its entirety for the technical descriptions and background information therein.

Recently introduced techniques based on a global, rather than local, formulation use the integral, rather than the differential, form of Maxwell equations. Such approaches differ from previous techniques in how they seek to solve the inverse problem (i.e., estimating a distribution of electrical properties from field-related measurements that depend on the distribution of electrical properties). However, such techniques are two-dimensional and are limited to extracting electrical properties, and have not yielded highly accurate results.

The embodiments described herein leverage the interaction between RF electromagnetic waves with biological tissue or other materials to ascertain electrical properties of tissue or other material. Maxwell's equations dictate the relationship between the shape of propagating RF fields and electrical conductivity, and permittivity of a sample. Thus, knowledge of RF field distributions inside a human body or other target may be used to calculate tissue electrical properties via Maxwell's equations.

More specifically, according to an embodiment, electrical properties of a tissue or other material are determined using Global Maxwell Tomography (GMT). GMT is a volume integral equation based technique for the extraction of electric properties from MR data. In GMT, B1+ and/or MR signal maps are iteratively simulated, adjusting the estimate of sample electrical properties at each iteration, until the error between simulated and measured B1+ and/or MR signal maps is below a specified tolerance. Beneficially, due to its global nature, GMT is not subjected to edge artifacts and can be performed in the case of high spatial resolutions, for example the resolution used in clinical MRI scans. In contrast, if high (clinical) resolution is used with 'local' methods as described above, the noise will increase substantially when taking first and second derivative data, precluding accurate estimation of electrical properties. By including transmit and receive phases in the model, GMT does not rely on symmetry assumptions. Employing the full MR signal in addition to B1+ allows for better numerical conditioning of GMT and to determine spin density and absolute phase of B1+, in addition to electrical properties.

FIG. 1 depicts a process involving GMT-based evaluation of electrical properties from a tissue or other material sample. As shown in FIG. 1, simulated data is produced in tandem with experimental data. An 'educated guess' or estimate is made of the material properties of a scanned object. From this estimate, a full electromagnetic simulation is used to obtain a simulated B1+ and/or MR signal map. The simulated B1+ and/or MR signal map is compared to a measured B1+ and/or MR signal map. Parameters such as relative permittivity and conductivity are then adjusted accordingly in the calculation to reduce a discrepancy between the simulation result and the measured values. Such a procedure may be repeated iteratively until such discrepancy is smaller than a defined tolerance, which may be similar to the noise level.

In particular, in the process shown in FIG. 1, a simulation is performed in tandem with experiments, as described in more detail. In particular, if a simulator model of one or more RF transmitters used for the experiments is available, then the incident field or fields of the one or more transmitters is/are calculated directly. If the simulator model is not available, then basis functions are defined in order to model the incident field or fields. The weights to combine the basis functions in order to model the correct incident field or fields could be found by including them as additional unknowns in the iterative framework. Then, an electromagnetic field distribution in the tissue or other material is calculated from the incident field or fields. Following the calculation, simulation data is processed in order to generate field-related quantities, such as B1+ and/or MR signal maps.

Referring again to FIG. 1, experimentation is performed in order to transmit a plurality of stimulations (e.g., RF excitations) to tissue or other material using one or more transmitters. The plurality of signals associated with the excited tissue or material and the transmitted stimulations are measured. Following the measurements, the measured signals are processed to generate field-related quantities, such as B1+ and/or MR signal maps. Once field-related quantities are generated from the simulation and experimental procedures, the quantities are compared to each other. If the quantities are the same or approximately the same (e.g., no more than 1%-3% difference), then it is determined that the electrical properties were correctly estimated in the simulation and a map or image is generated of one or more electrical properties of the tissue or material. If the quantities are not equivalent and instead differ (e.g., if they differ by a threshold, such as by more than 5%, or more than 10%), then new values for tissue electrical properties are calculated based on the previous step of the iteration, and updated field-related quantities are generated by processing the new simulation data, i.e., with the updated estimate of electrical properties. In this manner, the foregoing process allows for 'learning' from the errors and/or results associated with a prior estimation.

The approach of FIG. 1 employs a fast volume integral equation solver, the Magnetic Resonance Integral Equation (MARIE), available at http://thanospol.github.io/MARIE, designed for highly inhomogeneous, lossy dielectric media, and which enables rapid full-domain electromagnetic simulation. The integral equation algorithm obtains an equivalent current distribution that matches the incident field data via an iterative solving procedure for the resulting second-kind integral equation system. Similarly, a gradient of a cost function that is minimized is derived analytically in terms of elementary mathematical operators that make up the integral equation formula, enabling a rapid reduction in error.

In order to solve the systems of equations efficiently, a biconjugate gradient stabilized method is used. Such a method may use a quasi-Newton-type algorithm for large-scale unconstrained optimization (e.g., Limited-Memory Broyden-Fletcher-Goldfarb-Shanno (BFGS) or L-BFGS). Solving for the equivalent currents and for the gradient involves solving an adjoint formulation that uses the same operators. Solving the adjoint formulation forms the 'inner loop' of a formulation according to an embodiment of the present disclosure, whereas the quasi-Newton stepping forms the 'outer loop' of the algorithm. The GMT formulation is described below in more detail.

Notation and Definitions

In the following equations, f is the operating frequency, j is the imaginary unit, and $\omega=2\pi f$. Superscripted T and * indicate transposition and conjugate-transposition, respectively. $\odot$ and $\otimes$ are the Hadamard and Kronecker product operators, respectively. $|x|^2 \equiv x \otimes \bar{x}$ and diag (x) denotes diagonalization of x.

Cost Function

Electrical property estimation is performed with the decision variables being complex relative permittivities within the scatterer, namely $\epsilon \in \mathbb{C}^N$, where N is the number of voxels within the scatterer. The cost function is set to be:

$$f(\epsilon) = \sqrt{\frac{\sum_k \sum_n \left\| b_n \odot \bar{b}_k - \hat{b}_n \odot \hat{\bar{b}}_k \right\|_2^2}{\sum_k \sum_n \left\| \hat{b}_k \odot \hat{b}_n \right\|_2^2}} \qquad (1)$$

where k and n enumerate distinct measurements of the same object, $\hat{b}_k \in \mathbb{C}^N$ and $b_k \in \mathbb{C}^N$ indicate the simulated and measured maps, respectively, of the right-handed circularly polarized magnetic flux densities that MR transmit coils induce (also known as $B_1+$ field). Note that in the case of multiple transmitters, only the relative phases between the different $B_1+$ fields can be measured. The denominator is a weighting parameter that is used to normalize the cost function.

Volume Integral Equations

Any suitable electromagnetic field computation tool can be used to calculate the simulated quantities in the cost function. For example, the Magnetic Resonance Integral Equation suite (MARIE) could be used to obtain $|\hat{b}_j^+|$ from the relative permittivities $\epsilon$, and the incident electric fields $e_{inc,k} \in \mathbb{C}^{3N}$. The algorithm in MARIE uses the JVIE formulation proposed by A. Polimeridis et al., *Stable FFT-JVIE solvers for fast analysis of highly inhomogeneous dielectric objects*, J. Comp. Physics, Vol. 269, 15 Jul. 2014, p. 280-296. The JVIE formulation obtains equivalent current densities $j_k \in \mathbb{C}^{3N}$ by solving the system:

$$Aj_k = (P_\epsilon \Delta - P_x N) j_k = C_e P_x e_{inc,k}. \quad (2)$$

The map of electric susceptibilities is represented by $\chi \equiv \epsilon - 1$, the Gramian $\Delta$ is equal to the volume of each voxel, and the integro-differential operator N encapsulates the Green function, the constant $c_e = j\omega\epsilon_0$, and the linear operator:

$$P_x = \mathrm{diag}([111]^T \otimes x). \quad (3)$$

The total circularly polarized magnetic flux density in trial k is given by:

$$b_k^+ = F\mu_0(h_{inc,k} + Kj_k), \quad (4)$$

where $F = [1\ j\ 0]^T \otimes I_N$ and K is the complementary operator of N. The only approximation that is made is that the scatterer does not significantly perturb the current distributions on the coils.

Analytic Gradient of Cost Function

The total co-gradient is given by:

$$g(\epsilon) = \frac{\partial f}{\partial \epsilon} = -\frac{\mu_0 Q^T}{f(\epsilon)} \left( \frac{\sum_k \overline{\psi}_k \odot \gamma_k \oslash \overline{\epsilon^2}}{\sum_k \sum_n \||\hat{b}_k \odot \hat{b}_n|\|_2^2} \right)^*, \quad (5)$$

where $g(\epsilon) \in \mathbb{C}^{1 \times N}$ and $Q = [1\ 1\ 1]^T \otimes I_N$. The vector $\gamma_k \in \mathbb{C}^{3N}$ involves one adjoint solution of the original system:

$$\gamma_k = A^{-*} K^* F^* [\hat{b}_k \odot (\Sigma_n \overline{b_n} \odot b_n) - b_k \odot \Sigma_n(|\hat{b}_n|^2)]. \quad (6)$$

Additionally, the vector $\psi_k \in \mathbb{C}^{3N}$ is given by $$\psi_k = c_e e_{inc,k} - (\Delta - N) j_k. \quad (7)$$

Cost Function of Regularizer

Noise is addressed by adding a regularizer to the original cost function. A weight is chosen to properly weigh the regularizer with respect to the cost function. The cost function of this regularizer is given by:

$$f_0(\epsilon) = \frac{\langle 1 - e^{-\left(\frac{\Delta_x \epsilon}{a}\right)^2} \rangle + \langle 1 - e^{-\left(\frac{\Delta_y \epsilon}{a}\right)^2} \rangle + \langle 1 + e^{-\left(\frac{\Delta_z \epsilon}{a}\right)^2} \rangle}{3} \quad (8)$$

where $\epsilon$ is the complex permittivity (decision variables) and the constant $\alpha$ controls the placement of the transition from 0 to 1 of the regularizer. The corresponding gradient of the regularizer cost function is:

$$g_0(\epsilon) = \frac{1}{3a^2 N} \left\{ \left[ (\Delta_x \epsilon) \odot e^{-\left(\frac{\Delta_x \epsilon}{a}\right)^2} \right]^* \Delta_x + \left[ (\Delta_y \epsilon) \odot e^{-\left(\frac{\Delta_y \epsilon}{a}\right)^2} \right]^* \Delta_y + \left[ (\Delta_z \epsilon) \odot e^{-\left(\frac{\Delta_z \epsilon}{a}\right)^2} \right]^* \Delta_z \right\}, \quad (9)$$

in which N indicates the number of voxel in the scatterer (i.e., the sample).

Clustering of Electrical Properties

Based on the distribution of electrical properties after a single run of the GMT algorithm, to enhance results, a clustering algorithm can be used to segment the sample into bitmasks $M = [M_1\ M_2\ \ldots\ M_N]$ such that $$M_k \cap M_n = \begin{cases} \varnothing, k \neq n \\ M_k, k = n \end{cases}$$

and $M_0 = \cup_{k=1}^N M_k$, where $M_0$ is the original scatterer. Once the clusters have been obtained, the permittivities may be expressed as $\epsilon = M\alpha$, where $\alpha$ is a set of weights for each cluster, effectively containing the average value of the electrical properties $\epsilon$ over that cluster. The GMT algorithm is then run over $\alpha$ instead of the full $\epsilon$, with the same cost functions and the gradients adjusted such that:

$$\frac{\partial f}{\partial \alpha} = \frac{\partial f}{\partial \epsilon} \frac{\partial \epsilon}{\partial \alpha} = \frac{\partial f}{\partial \epsilon} M \quad (10)$$

MR Signal-Based Cost Function

While the cost function in Equation 1 compares measured and calculated maps of the $B_1+$ field, a different cost function may be used based on the received MR signal:

$$f'(\epsilon) = \sqrt{\frac{\sum_k \sum_l \|\hat{s}_{kl} - m \odot b_k^+ \odot b_l^- \odot \mathrm{sinc}(\alpha|b_k^+|)\|_2^2}{\sum_k \sum_l \|\hat{s}_{kl}\|_2^2}} \quad (11)$$

where $\hat{s}_{kl}$ is the signal resulting from the $k^{th}$ transmit configuration and $l^{th}$ receive coil, m is the complex-valued magnetization which describes the spin density and the background phase, $b_k^+$ is the $k^{th}$ transmit right-handed circularly polarized flux density, $b_l^-$ is the $l^{th}$ receive left-handed circularly polarized flux density, and $\alpha$ dictates the flip angle dependence on the intensity of $|b_k^+|$.

The gradient of the signal-based cost function is given by:

$$\frac{\partial f'}{\partial \epsilon} = -\frac{\mu_0 Q^T}{2f(\epsilon)(\sum_k \sum_l \|\hat{s}_{kl}\|_2^2)} \left[ \left( \sum_k D(\overline{\psi}_k^+) A^{-*} K^* F^* \left( \sum_l r_{kl}^+ \right) \right) + \left( \sum_l D(\overline{\psi}_l^-) A^{-*} K^* F^T \left( \sum_k r_{kl}^- \right) \right) \right], \quad (12)$$

where:

$$\sum_l r_{kl}^+ = m \odot W_k^- \odot \left(\sum_l b_l^- \odot \bar{\delta}_{kl}\right) + \bar{m} \odot \overline{W_k^+} \odot \left(\sum_l \overline{b_l^-} \odot \delta_{kl}\right) \quad (13)$$

$$\sum_k \overline{r_{kl}^-} = m \odot \left(\sum_k b_k^+ \odot \mathrm{sinc}(\alpha|b_k^+|) \odot \bar{\delta}_{kl}\right)$$

$$W_k^+ = \frac{1}{2}[\cos(\alpha|b_k^+|) + \mathrm{sinc}(\alpha|b_k^+|)]$$

$$W_k^- = \frac{1}{2}[\cos(\alpha|b_k^+|) - \mathrm{sinc}(\alpha|b_k^+|)] \odot e^{j2\phi_k^+}$$

The cost function in Equation 11 may be used in place of or in combination with the cost function in Equation 1, in order to improve the numerical conditioning of the GMT algorithm and to enable to determine absolute phase and spin density, in addition to electrical properties. If both the MR signal and $B_1+$ are used, the comprehensive cost function would be a weighted combination of the two cost functions:

$$f''(\epsilon) = \tau f(\epsilon) + (1-\tau)f'(\epsilon), \quad (14)$$

where $\tau$ is a weighting coefficient that can have values between 0 and 1.

FIGS. 2A-2D and 3A-3B depict results of simulations performed using the GMT formulation described above. A and A* were solved using the biconjugate gradient stabilized method, and quasi-Newton L-BFGS was used. In both examples, f was set to 297.2 MHz, the frequency of operation of a typical 7 T scanner, and eight scans were used, each with a distinct, naïve coil configuration. Additionally, $\epsilon_i$, $\epsilon_T$, and $\epsilon_F$ refer to initial, desired, and inferred complex permittivity maps, respectively. In each case, a simulated $\hat{b}_k$ map was generated using $\epsilon_T$.

In the implementation described above, the cost function seeks to minimize the error in estimates of $B_1+$, or s (signal), or a combination of both quantities. More specifically, it seeks to minimize the error in the square of the magnitude at each location within the sample. In order to condense a three-dimensional tensor of error to a scalar value, the square of each entry is summed in the error tensor. Further, multiple scans are handled by weighing and summing the measures of error across all scans.

Figure 2A:
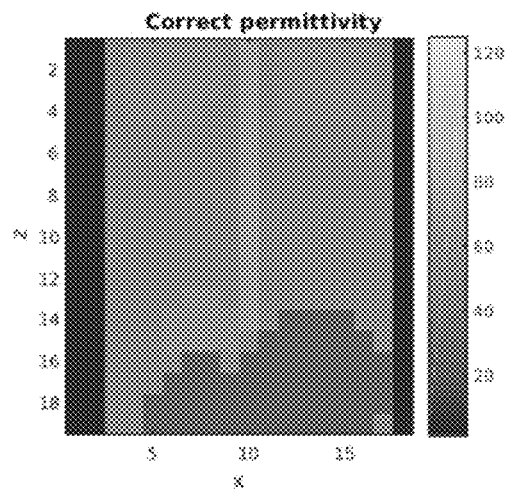
FIGS. 2A-2D illustrate exemplary simulations of reconstructed electrical properties of a tissue-mimicking numerical phantom according to an embodiment.
Figure 2B:
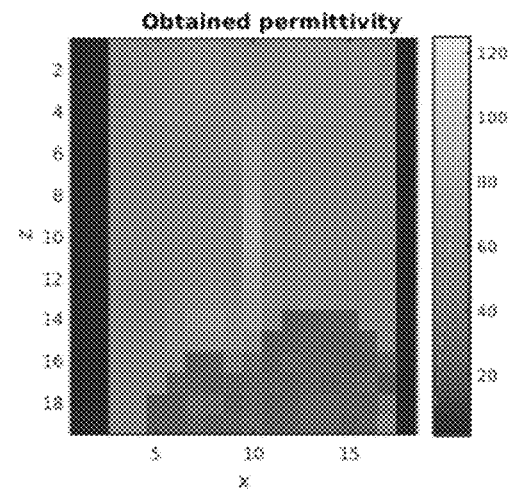
Figure 2C:
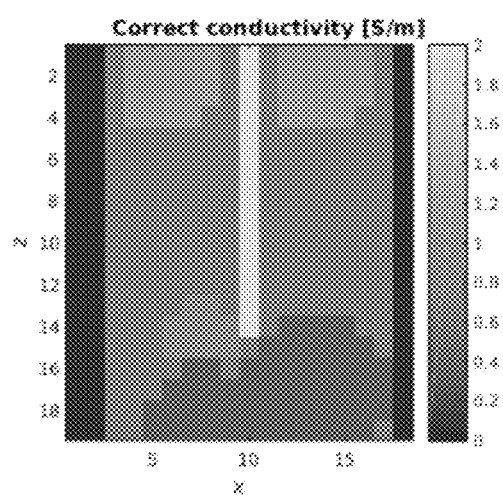
Figure 2D:
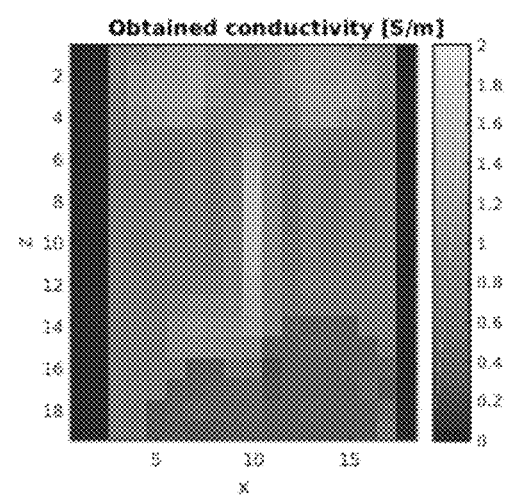

FIGS. 2A-2D depict reconstruction of electrical properties of a tissue sample according to an embodiment. FIG. 2A depicts the $\epsilon_R$ (i.e., relative permittivity) of a target, and FIG. 2B depicts the $\epsilon_R$ of the output, FIG. 2C depicts the conductivity of the target, and FIG. 2D depicts the conductivity of the output. An asymmetric numerical phantom was constructed with electric properties that mimic human tissue: $\epsilon_R \in (1,100)$ and $\sigma \in (0, 2 \text{ S/m})$. Each value in $\epsilon_i$ was set to the average of $\epsilon_T$. The algorithm terminated after $|\Delta f|/|f(\epsilon_i)|<10^{-8}$. The reconstruction was performed for a tissue-mimicking numerical phantom from a homogeneous guess, in the absence of noise, at a resolution of 9 mm, at an operating frequency of 297.2 MHz. As shown in FIGS. 2A-2D, the properties of all structures in the phantom were reconstructed correctly solely from B1+ data, although the edges are blurred, as is customary with local methods.

Figure 3A:
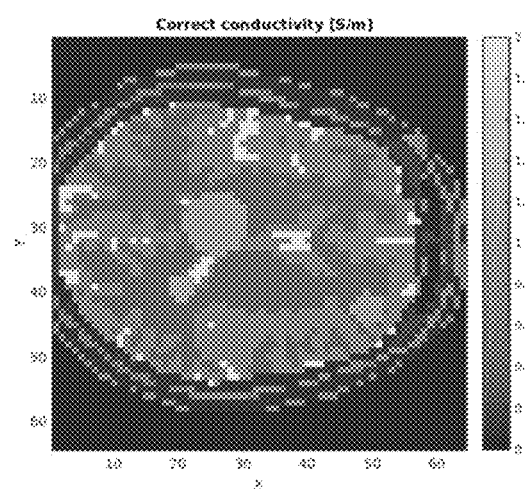
FIGS. 3A-3B illustrate electrical conductivity characterization of a numerical brain model according to an embodiment.
Figure 3B:
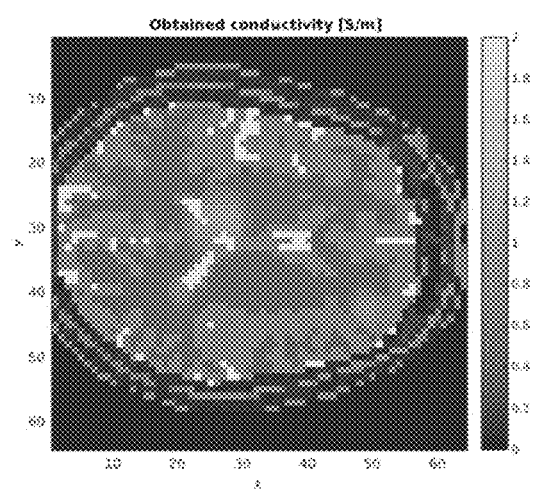

FIGS. 3A-3B depict results of an experiment to characterize electrical conductivity using artificial insertions of tumors. FIG. 3A depicts a target $\sigma$ with tumors, and FIG. 3B depicts an inferred $\sigma$ (started without tumors). In particular, a plurality of simulated tumors were inserted into a model of a human head. Starting from an initial estimate (an initial guess) that no tumors were present, the electrical properties and location of each tumor were inferred using GMT. Thus, $\epsilon_i$ was extracted from the head of an open-source Duke model, and $\epsilon_T$ was formed by inserting numerical tumors into $\epsilon_i$, with $\sigma \in [1.2 \text{ S/m}, 1.8 \text{ S/m}]$. Noise was added to $\hat{b}_k^+$ to achieve an SNR of 80. GMT terminated after $\|\Delta\epsilon\|_2/\|\epsilon_i\|_2 < 10^{-6}$.

The three tumors were artificially inserted into the open-source Duke head model, at a resolution of 3 mm and a frequency of 297.2 MHz. The relative permittivity and the conductivity of the tumors were set to values in the ranges (50, 60) and (1.1, 1.2) S/m, respectively. The initial estimate or guess is that of the default Duke head model itself, that is, the Duke model without any tumors. As shown in FIG. 3B, the tumors were correctly identified and the reconstructed electrical properties of these tumors were generally inferred correctly, with some blurring present. The method converged after 124 iterations.

Figure 4A:
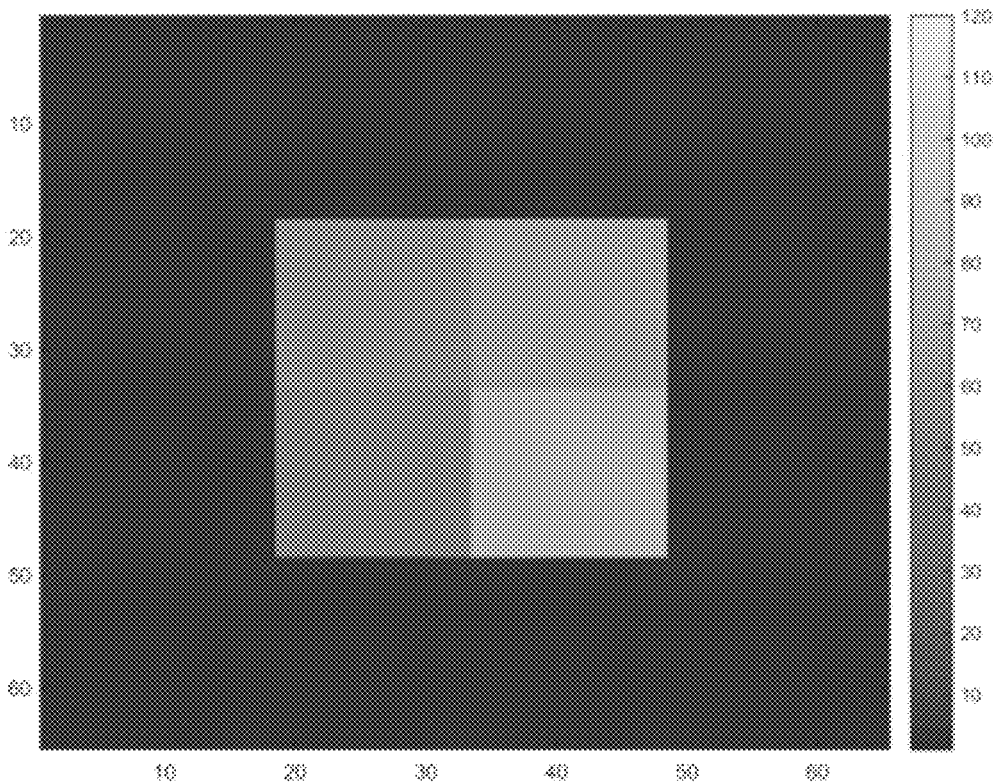
FIGS. 4A-4C illustrate relative permittivity maps for a four-compartment tissue-mimicking numerical phantom determined according to an embodiment, starting with a homogeneous estimation.
Figure 4A:
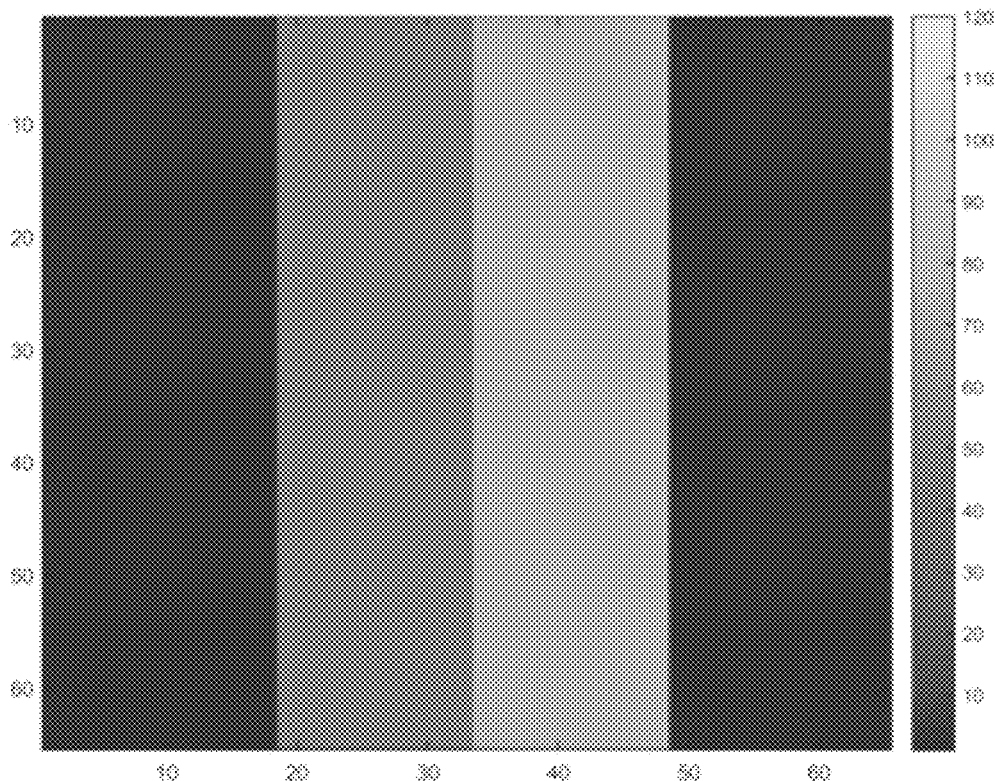
Figure 4B:
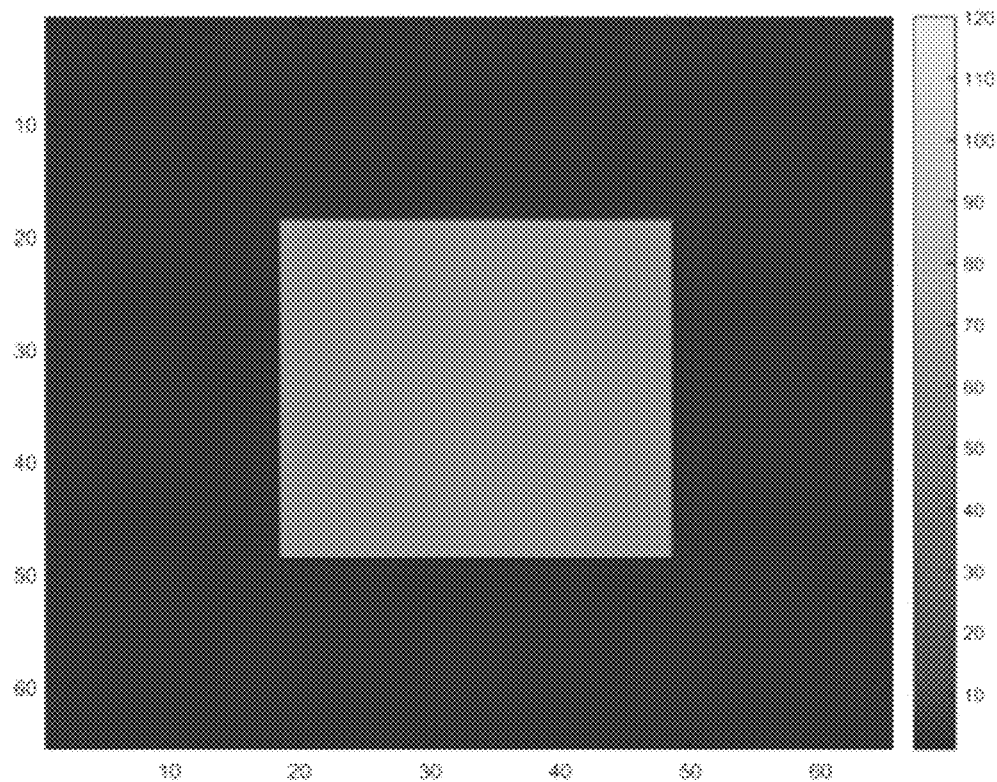
Figure 4B:
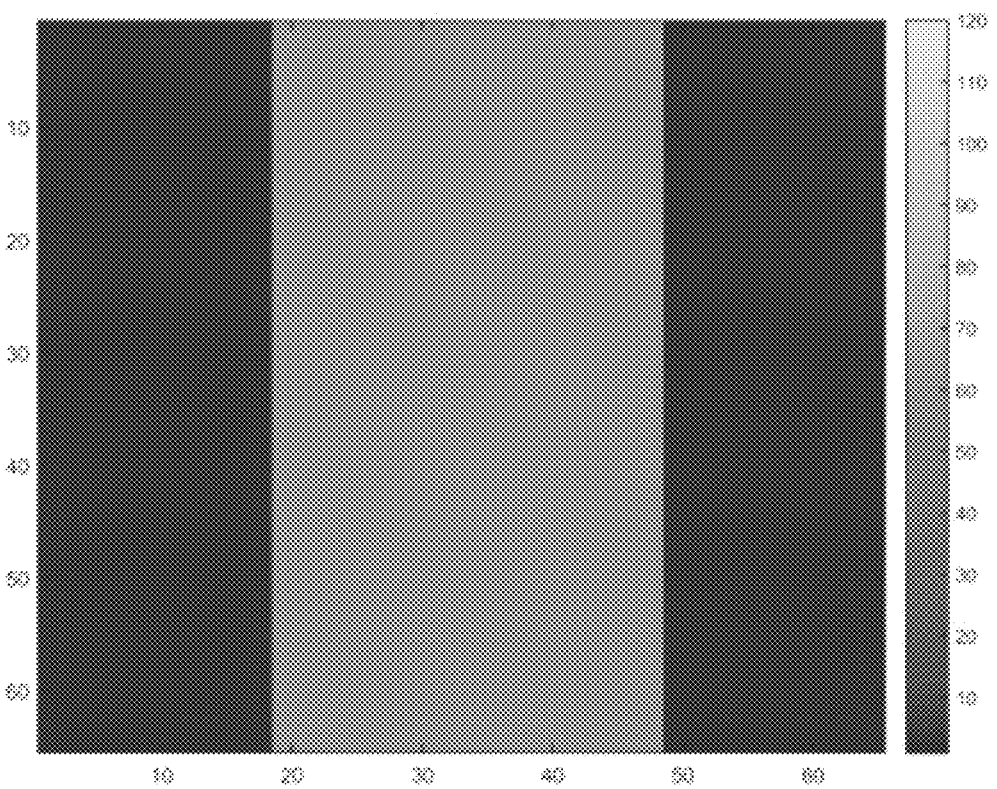
Figure 4C:
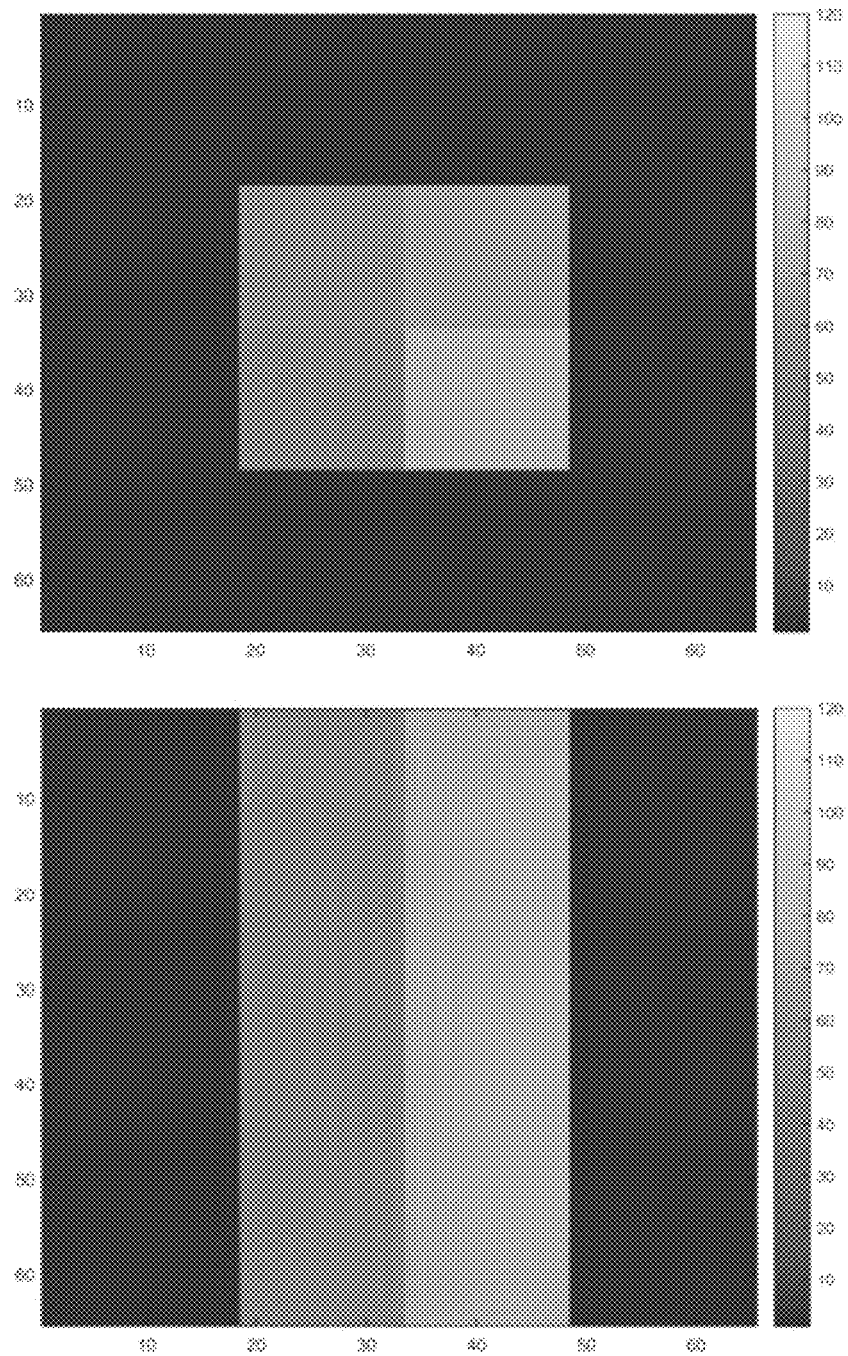

FIG. 4A-4C depict reconstruction of electrical permittivity of a tissue sample according to an embodiment. Specifically, FIG. 4A depicts the 'ground truth' permittivity, FIG. 4B depicts an initial guess, and FIG. 4C depicts a final reconstruction. The reconstruction was performed for a tissue-mimicking numerical phantom from the homogeneous guess, in the absence of noise, at a resolution of 3 mm, at an operating frequency of 297.2 MHz. Tissue-mimicking phantoms similar to the numerical phantom used in this embodiment are described, for example, in C. Ianniello, R. Brown, M. Cloos, Q. Duan, J. Walczyk, G. Wiggins, D. K. Sodickson and R. Lattanzi, *Sugar free tissue-mimicking MRI phantoms for improved signal-to-noise ratio*, 24th Annual Meeting of the International Society of Magnetic Resonance in Medicine, p. 2239. As shown in FIG. 4(a)-(c), the properties of all compartments in the phantom were reconstructed correctly solely from $B_1+$ data, with relative error $\le 1\%$ and without blurring or artifacts at the edges.

Figure 5A:
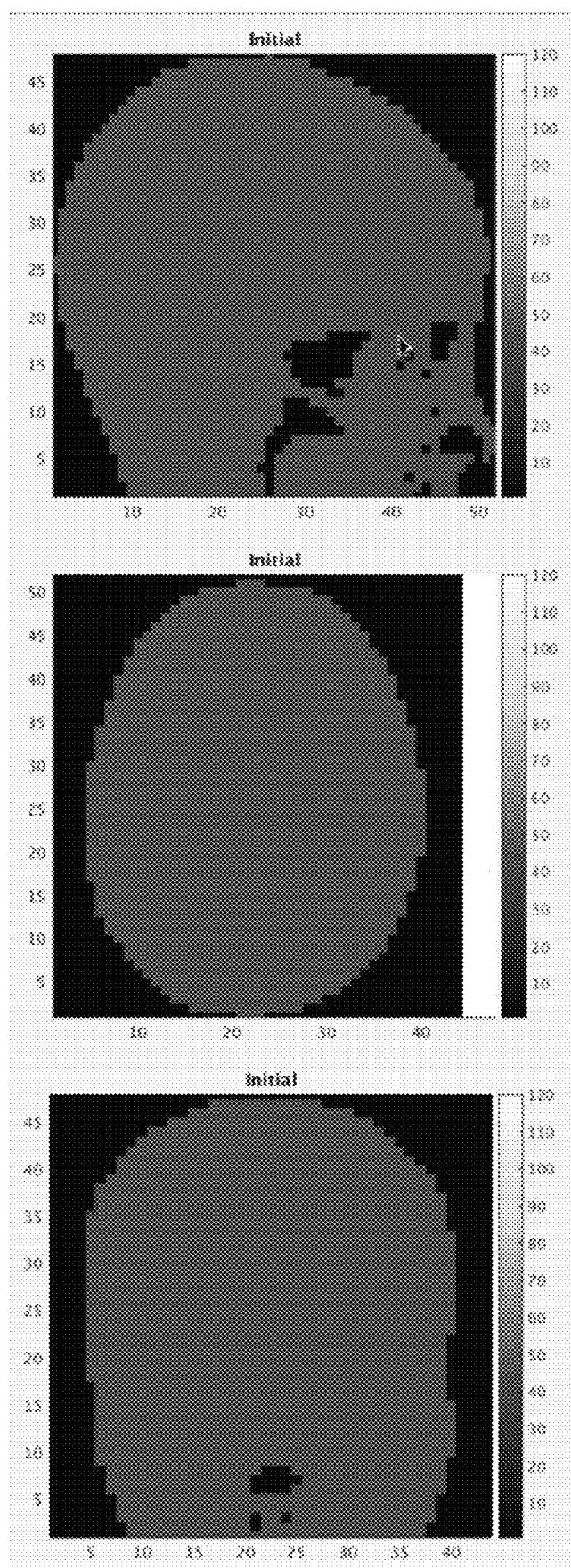
FIGS. 5A-5D illustrate relative permittivity maps for a numerical head model determined according to an embodiment, starting with a homogeneous estimation.
Figure 5B:
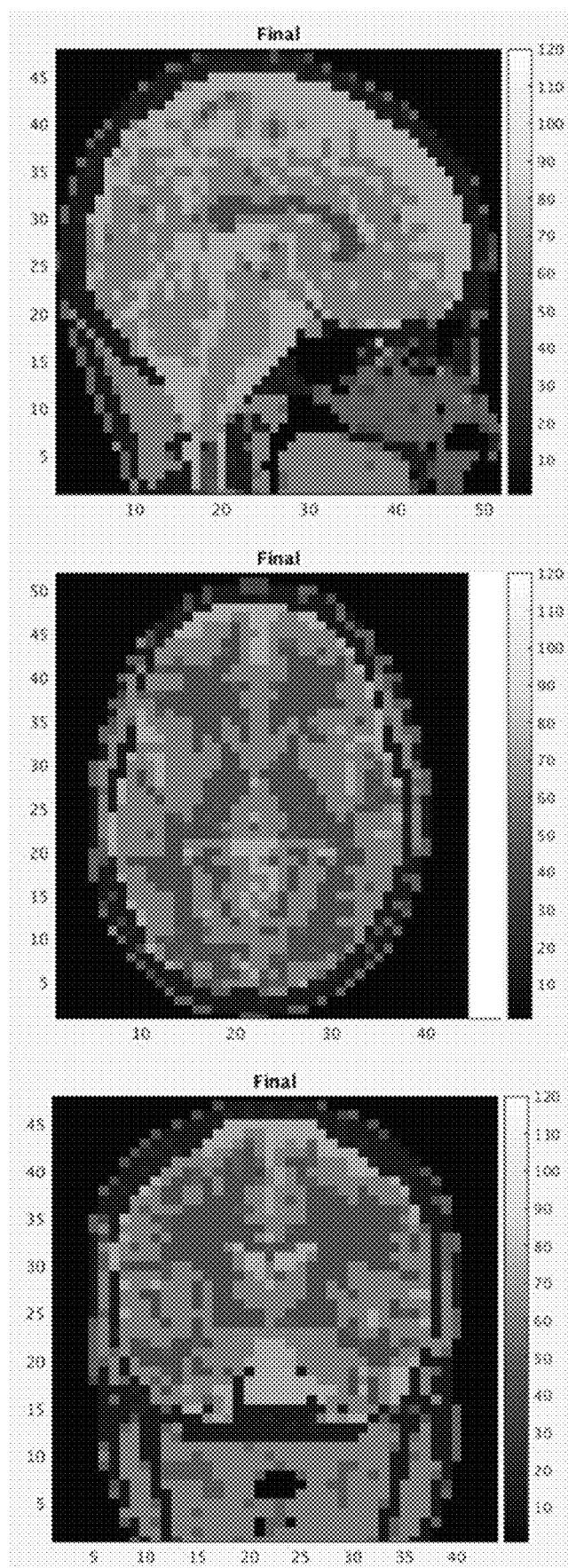
Figure 5C:
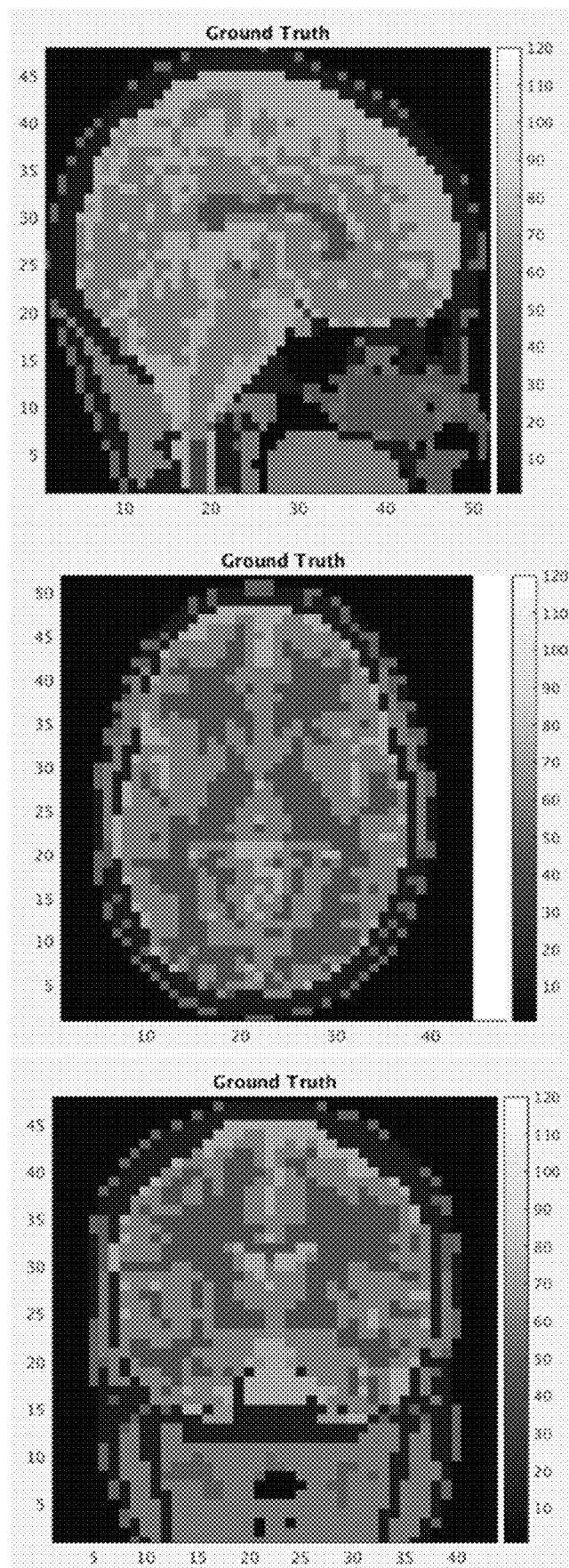
Figure 5D:
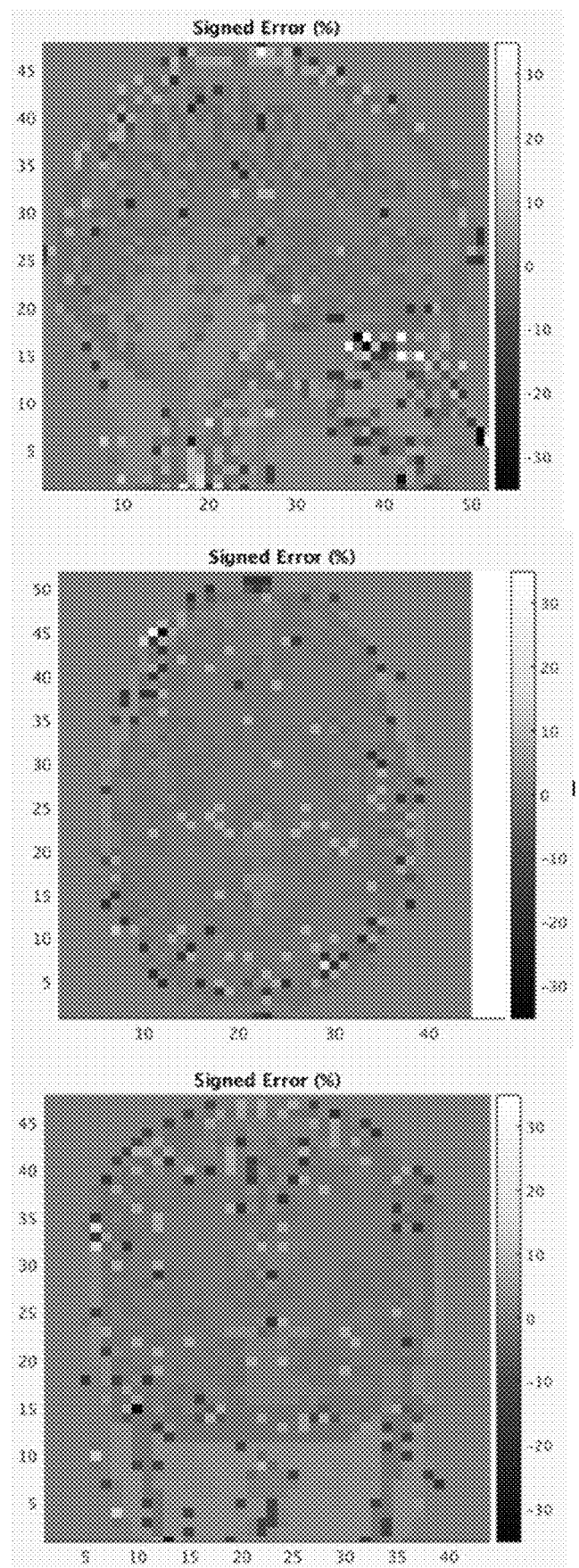

FIGS. 5A-5D illustrate relative permittivity maps for a numerical head model determined according to an embodiment, starting with a homogeneous estimation. Specifically, FIG. 5A depicts initial estimates of permittivity, FIG. 5B depicts final reconstructions, FIG. 5C depicts the 'ground truth' permittivity, and FIG. 5D depicts error percentages. The maps are obtained by similar methods as those shown in FIGS. 4A-4C, apart from the following differences. First, instead of a tissue-mimicking phenomenon, a numerical head model was used (the "Ella" model from the 'Virtual Family' Project, see Christ A., Kainz W., Hahn E. G., Honegger K., Zefferer M., Neufeld E., Rascher W., Janka R., Bautz W., Chen J., Kiefer B., Schmitt P., Hollenbach H. P., Shen J. X., Oberle M., and Kuster N., "The Virtual Family—Development of Anatomical CAD Models of two Adults and two Children for Dosimetric Simulations", Physics in Medicine and Biology, 55, n. 23-38 (2010)). Second, the isotropic voxel resolution was larger (4 mm as opposed to 3 mm). Third, a clustering algorithm (as shown in Equation 10) was used.

In particular, FIG. 5D illustrates relative error percentages between the final reconstruction (FIG. 5B) and the ground truth (FIG. 5C). The uppermost, middle, and bottom maps in each of FIGS. 5A-5D correspond to three 'slices' cutting through the center of the head, which represent three anatomical planes. From top to bottom, the sagittal, axial and coronal planes are shown. Notably, the obtained results are nearly perfect reconstructions of electrical properties for most voxels within the brain region.

The GMT technique of the embodiments indicated that when a guess or estimate was completely incorrect, and no assumptions were made about electrical properties of materials within a phantom, a successful convergence was achieved to a close approximation of the true property distribution. Further, when an initial guess was close to the actual values but overlooked important yet unknown elements, i.e., the artificial tumors, these were successfully reconstructed, even in the presence of noise. No edge artifacts were found in either case. The observed blurring may be attributable to conditioning of the 'outer loop,' that is, the quasi-Newton stepping loop. The outer loop may be preconditioned to achieve faster convergence, and proper regularizations, such as additive total variations, may be incorporated in order to deal with the impact of noise.

Figure 6:
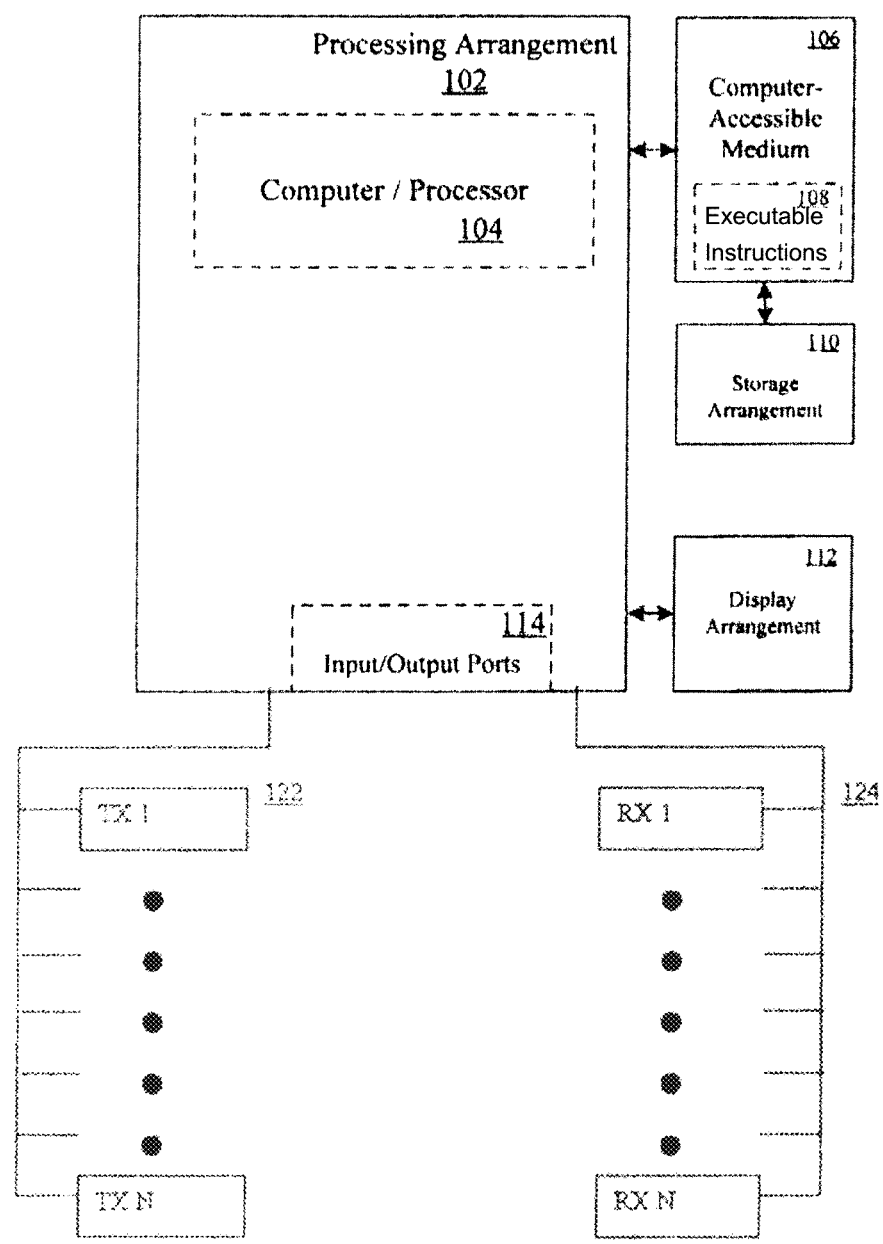
FIG. 6 illustrates a system including a plurality of radiofrequency transmitters and detectors, and a processing arrangement according to an embodiment.

FIG. 6 shows a block diagram of a system according to an embodiment. The embodiment shown in FIG. 6 includes a system for determination of electrical properties of a tissue or other material. For example, the methods of various embodiments may be performed by transmitters 122 (TX 1 through TX N), receivers 124 (RX 1 through RX N), and a processing arrangement 102 including a computing arrangement. The transmitters 122 are configured to create stimulations applied to the tissue or material. The receivers 124 are configured as detectors having radiofrequency coils to measure signals. The processing and computing arrangement (a computing device) have a tangible computer-readable medium operatively connected to a processor, so as to execute programmable coded instructions. The processor is configured to execute instructions to carry out procedures in accordance with the techniques described herein. Such a processing arrangement 102 may be part of, but is not limited to, a computer/processor 104 that can include one or more microprocessors, one or more microcomputers and/or one or more microcontrollers, and use instructions stored on a computer-accessible medium 106 (e.g., RAM, ROM, hard drive, or other storage device). The computer/processor 104 is configured to perform a comparison of the electromagnetic field-related quantities obtained from processing the measured signals to simulated electromagnetic field-related quantities. The computer/processor 104 is further configured to execute the GMT formulation and simulations described above.

As shown in FIG. 6, the computer-accessible medium 106 (e.g., as described herein above, a storage device such as a hard disk, floppy disk, memory stick, CD-ROM, RAM, ROM, etc., or a collection thereof) can be provided (e.g., in communication with the processing arrangement 102). The computer-accessible medium 106 can contain executable instructions 108 thereon. The computer-accessible medium 106 may include a memory having storage space, and may be configured to store data such as signal information from the transmitters 122 and receivers 124. In addition, or alternatively, a storage arrangement 110 can be provided separately from the computer-accessible medium 106, which can provide the instructions to the processing arrangement 102 so as to configure the processing arrangement to execute certain exemplary procedures, processes and methods, as described above, for example.

Further, the exemplary processing arrangement 102 can be provided with or include an input/output arrangement 114, which can include, e.g., a wired network, a wireless network, the internet, an intranet, a data collection probe, a sensor, etc. As shown in FIG. 6, the exemplary processing arrangement 102 can be in communication with an exemplary display arrangement 112, which, according to certain exemplary embodiments of the present disclosure, can be a touch-screen configured for inputting information to the processing arrangement in addition to outputting information from the processing arrangement, for example. Further, the exemplary display 112 and/or a storage arrangement 110 can be used to display and/or store data in a user-accessible format and/or user-readable format.

Various embodiments are described in the general context of methods, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software embodiments may be realized with programming techniques including rule based logic and other logic to accomplish the various acquisition, analysis and compression steps, for example. It should also be noted that the words "component" and "module," as used herein and in the claims, are intended to encompass embodiments using one or more lines of software code, and/or hardware embodiments, and/or equipment for receiving manual inputs.

Certain embodiments described above achieve various advantages, including higher treatment efficacy by employing subject-specific data. The techniques described herein may be applied to a wide range of applications so as to allow further analysis of electrical properties of tissues in a non-invasive manner.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments or implementations has been presented for purposes of illustration and of description. It is not intended to be exhaustive or limiting with respect to the precise form disclosed, and modifications and variations are possible in light of the above teachings or may be acquired from practice of the disclosed embodiments. Therefore, the above embodiments should not be taken as limiting the scope of the invention.

What is claimed is:

1. A method for determining at least one electrical property of at least one target, comprising:
   transmitting, to the at least one target, a plurality of stimulations via one or more transmitters,
   measuring signals associated with the stimulated target,
   processing the measured signals to obtain electromagnetic field-related quantities,
   generating a numerical model of incident electromagnetic fields of the one or more transmitters,
   using the numerical model to calculate a first simulated electromagnetic field distribution in the at least one target based on initially estimated or otherwise assigned values of electrical properties of the at least one target,
   generating simulated electromagnetic field-related quantities from the first simulated electromagnetic field distribution,
   evaluating whether a difference between the electromagnetic field-related quantities obtained from processing of the measured signals and the simulated electromagnetic field-related quantities generated from the first simulated electromagnetic field distribution exceeds a threshold, and when the difference exceeds the threshold:
  using the numerical model to calculate a second simulated electromagnetic field distribution after adjusting one or more estimated values of electrical properties of the at least one target,
  generating simulated electromagnetic field-related quantities from the second simulated electromagnetic field distribution, and
  evaluating whether a difference between the electromagnetic field-related quantities obtained from processing of the measured signals and the simulated electromagnetic field-related quantities generated from the second simulated electromagnetic field distribution exceeds the threshold, iteratively performing one or more of the above steps until the difference is less than or equal to the threshold.

2. The method of claim 1, further comprising:
upon determining that the electromagnetic field-related quantities obtained from processing the measured signals are equivalent to the simulated electromagnetic field-related quantities, generating at least one map or image of the at least one electrical property of the at least one target.

3. The method of claim 1, wherein the simulated electromagnetic field-related quantities are generated by defining basis functions to model incident electromagnetic fields of the one or more transmitters, and calculating an electromagnetic field distribution in the at least one target from the incident electromagnetic fields and estimated values of electrical properties of the at least one target.

4. The method of claim 1, wherein the at least one target is a human tissue or non-tissue material.

5. The method of claim 1, wherein the plurality of stimulations are RF excitations.

6. The method of claim 1, wherein the electromagnetic field-related quantities include at least one of B1+ or an MR signal map.

7. The method of claim 1, wherein using the numerical model comprises using the numerical model together with global Maxwell's equations.

8. A non-transitory computer readable medium including instructions thereon that are accessible by a processing arrangement, wherein, when the processing arrangement executes the instructions, the processing arrangement is configured to:
  cause one or more transmitters to transmit, to at least one target, a plurality of stimulations,
  measure signals associated with the stimulated target,
  process the measured signals to obtain electromagnetic field-related quantities,
  generate a numerical model of incident electromagnetic fields of the one or more transmitters,
  use the numerical model to calculate a first simulated electromagnetic field distribution in the at least one target based on initially estimated or otherwise assigned values of electrical properties of the at least one target,
  generate simulated electromagnetic field-related quantities from the first simulated electromagnetic field distribution,
  evaluate whether a difference between the electromagnetic field-related quantities obtained from processing of the measured signals and the simulated electromagnetic field-related quantities generated from the first simulated electromagnetic field distribution exceeds a threshold, and when the difference exceeds the threshold:
  use the numerical model to calculate a second simulated electromagnetic field distribution after adjusting one or more estimated values of electrical properties of the at least one target,
  generate simulated electromagnetic field-related quantities from the second simulated electromagnetic field distribution, and
  evaluate whether a difference between the electromagnetic field-related quantities obtained from processing of the measured signals and the simulated electromagnetic field-related quantities generated from the second simulated electromagnetic field distribution exceeds the threshold, iteratively perform one or more of the above steps until the difference is less than or equal to the threshold.

9. The computer readable medium of claim 8, wherein the processing arrangement is further configured to:
upon determining that the electromagnetic field-related quantities obtained from processing the measured signals are equivalent to the simulated electromagnetic field-related quantities, generate at least one map or image of the at least one electrical property of the at least one target.

10. The computer readable medium of claim 8, wherein the simulated electromagnetic field-related quantities are generated by defining basis functions to model incident electromagnetic fields of one or more transmitters, and using the model to calculate an electromagnetic field distribution in the at least one target from the incident electromagnetic fields.

11. The computer readable medium of claim 8, wherein the signals are detected in at least one radiofrequency receiver coil.

12. The computer readable medium of claim 8, wherein the at least one target is a human tissue or non-tissue material.

13. The computer readable medium of claim 8, wherein the numerical model is used together with global Maxwell's equations.

14. A system for determining at least one electrical property of at least one target, comprising:
  one or more transmitters configured to transmit a plurality of stimulations to the at least one target,
  a signal detector configured to measure signals associated with the stimulated target,
  a computing device configured to:
    process the measured signals to obtain electromagnetic field-related quantities, and
    generate a numerical model of incident electromagnetic fields of the one or more transmitters,
    use the numerical model to calculate a first simulated electromagnetic field distribution in the at least one target based on initially estimated or otherwise assigned values of electrical properties of the at least one target,
    generate simulated electromagnetic field-related quantities from the first simulated electromagnetic field distribution,
    evaluate whether a difference between the electromagnetic field-related quantities obtained from processing of the measured signals and the simulated electromagnetic field-related quantities generated from the first simulated electromagnetic field distribution exceeds a threshold, and when the difference exceeds the threshold:
use the numerical model to calculate a second simulated electromagnetic field distribution after adjusting one or more estimated values of electrical properties of the at least one target,
generate simulated electromagnetic field-related quantities from the second simulated electromagnetic field distribution, and
evaluate whether a difference between the electromagnetic field-related quantities obtained from processing of the measured signals and the simulated electromagnetic field-related quantities generated from the second simulated electromagnetic field distribution exceeds the threshold, iteratively perform one or more of the above steps until the difference is less than or equal to the threshold.

15. The system of claim 14, wherein the computing device is configured to:
upon determining that the electromagnetic field-related quantities obtained from processing the measured signals are equivalent to the simulated electromagnetic field-related quantities, generating at least one map or image of the at least one electrical property of the at least one target.

16. The system of claim 14, wherein the computing device is configured to use the numerical model together with global Maxwell's equations.

\* \* \* \* \*